United States Patent
Kunishima et al.

(10) Patent No.: US 9,126,954 B2
(45) Date of Patent: Sep. 8, 2015

(54) HYDROXY GROUP PROTECTING AGENT AND HYDROXY GROUP PROTECTION METHOD

(71) Applicants: Munetaka Kunishima, Kanazawa (JP); Hikaru Fujita, Kanazawa (JP); Kohei Yamada, Kanazawa (JP)

(72) Inventors: Munetaka Kunishima, Kanazawa (JP); Hikaru Fujita, Kanazawa (JP); Kohei Yamada, Kanazawa (JP)

(73) Assignee: NATIONAL UNIVERSITY CORPORATION KANAZAWA UNIVERSITY, Kanazawa-shi, Ishikawa (JP)

( * ) Notice: Subject to any disclaimer, the term of this patent is extended or adjusted under 35 U.S.C. 154(b) by 0 days.

(21) Appl. No.: 14/359,183

(22) PCT Filed: Nov. 16, 2012

(86) PCT No.: PCT/JP2012/079834
§ 371 (c)(1),
(2) Date: May 19, 2014

(87) PCT Pub. No.: WO2013/073681
PCT Pub. Date: May 23, 2013

(65) Prior Publication Data
US 2014/0343281 A1    Nov. 20, 2014

(30) Foreign Application Priority Data

Nov. 18, 2011  (JP) .................................. 2011-253002

(51) Int. Cl.
*C07D 251/34* (2006.01)
*C07D 251/30* (2006.01)
*C07C 41/14* (2006.01)
*C07B 51/00* (2006.01)
*C07C 67/24* (2006.01)
*C07C 67/29* (2006.01)
*C07C 67/62* (2006.01)
*C07D 251/26* (2006.01)

(52) U.S. Cl.
CPC .............. *C07D 251/30* (2013.01); *C07B 51/00* (2013.01); *C07C 41/14* (2013.01); *C07C 67/24* (2013.01); *C07C 67/29* (2013.01); *C07C 67/62* (2013.01); *C07D 251/26* (2013.01); *C07D 251/34* (2013.01); *C07C 2101/14* (2013.01); *C07C 2103/74* (2013.01)

(58) Field of Classification Search
CPC .............................. C07D 251/34; C07D 251/30
USPC ......................................................... 544/219
See application file for complete search history.

(56) References Cited

U.S. PATENT DOCUMENTS

| 3,395,147 | A | * | 7/1968 | Cornell, Jr. .................... 544/219 |
| 3,923,621 | A | * | 12/1975 | Murayama et al. ........... 525/276 |
| 2007/0155983 | A1 | | 7/2007 | Ikemoto |

FOREIGN PATENT DOCUMENTS

| GB | 1563354 | * | 3/1980 |
| JP | WO2005/014508 A | | 2/2005 |
| JP | 2011057559 A | * | 3/2011 |

OTHER PUBLICATIONS

Srinivas K et al., Bioorganic & Medicinal Chemistry Letters 15 (2005) 1121-1123.*
PCT, "International Search Report for International Application No. PCT/JP2012/079834", Jan. 29, 2013.

* cited by examiner

Primary Examiner — Venkataraman Balasubramanian
(74) Attorney, Agent, or Firm — Manabu Kanesaka

(57) ABSTRACT

To provide: a hydroxy group protecting agent which is stable and easy to use, does not have carcinogenicity, a tearing property or the like, and is inexpensive; and a hydroxy group protection method which enables the protection of a hydroxy group under acidic conditions.
[Solution] A hydroxy group protecting agent in which at least one protecting group is bound to a nitrogen-containing electron-withdrawing heterocyclic ring through any one of an oxygen atom, a sulfur atom and a nitrogen atom. The heterocyclic ring is a triazine ring or the like, and the protecting group is a benzyl group or the like. Specifically, the hydroxy group protecting agent is 2,4,6-tribenzyloxy-1,3,5-triazine, 2,4,6-tris(4-methoxybenzyloxy)-1,3,5-triazine or the like. In addition, 2,4,6-tris(t-butoxy)-1,3,5-triazine or the like can also be used. For protecting a hydroxy group, a compound of interest which has a hydroxy group is reacted with the hydroxy group protecting agent under acidic conditions.

11 Claims, No Drawings

HYDROXY GROUP PROTECTING AGENT AND HYDROXY GROUP PROTECTION METHOD

RELATED APPLICATIONS

The present application is National Phase of International Application No. PCT/JP2012/079834 filed Nov. 16, 2012, and claims priority from Japanese Application No. 2011-253002, filed Nov. 18, 2011.

TECHNICAL FIELD

The present invention relates to a hydroxy group-protecting agent which is stable and easy to use, and further relates to a hydroxy group protection method for protecting a hydroxy group under an acidic condition.

BACKGROUND ART

For synthesis of an organic compound, for example in a case that reaction is inhibited by a hydroxy group, a case that the hydroxy group itself reacts, a case that the water solubility due to a hydroxy group of sugar or the like is lowered and the compound is rendered liposoluble, etc., the hydroxy group should be protected, and therefore various protecting groups have been used. A protecting group is a functional group for temporarily inducing a functional group disturbing synthetic reaction to be structurally inactive (protecting), and restoring it by desorption after reaction.

As the protecting group, various groups are known, and above all, benzyl group is very frequently used for reasons that it is considerably stable and hardly broken, that it is easy to eliminate by catalytic reduction (hydrogenation) using a metal of palladium or the like, that the deprotected compound can be easily purified (filtered and vaporized) because the compound becomes toluene after the elimination, etc.

As a method for introducing the benzyl group, a method using Williamson's ether synthesis as shown in Formula 1 is known, in which the reaction requires a basic condition, and cannot be applied to protection of alcohols comprising a functional group which is destabilized or decomposed in a basic condition in their molecules. In addition, a halogenated benzyl used as a hydroxy group-protecting agent (protecting agent) is carcinogenic and lachrymatory and thus undesirable in health or the like.

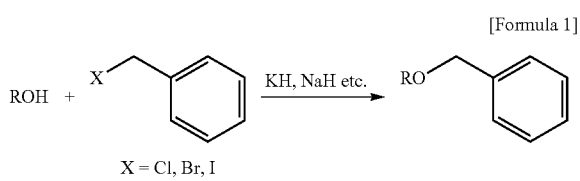

[Formula 1]

X = Cl, Br, I

For benzylating reaction using a halogenated benzyl, use of argentate is also considered, and for example, use of silver oxide (Ag$_2$O) as a catalyst allows the hydroxy group to be benzylated and protected even if not under a basic condition, as shown in Formula 2. However, silver oxide is expensive and has a great cost problem.

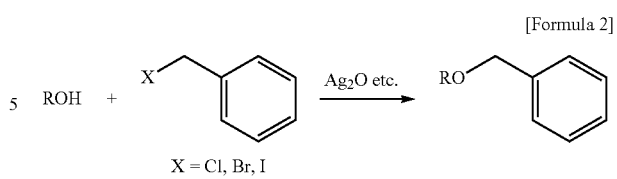

[Formula 2]

X = Cl, Br, I

Meanwhile, for the introduction of the benzyl group under an acidic condition, for example a method using benzyltrichloroacetimidate as shown in Formula 3 has been proposed. However, said benzyltrichloroacetimidate has disadvantages that it is easy to hydrolyze and susceptible to heat and moisture, thus handling is troublesome, and its price is high.

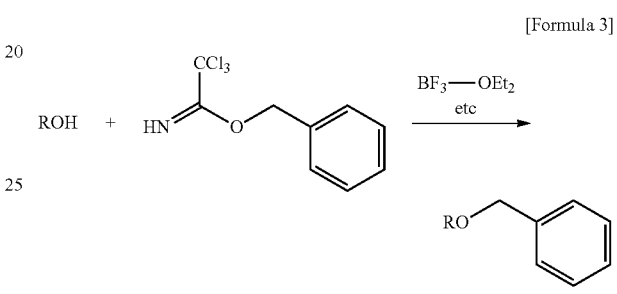

[Formula 3]

From such situations, methods in which the hydroxy group can be stably protected under an acidic condition have been studied. For example, protection of the hydroxy group by an acetal-type protecting group is proposed in Patent Document 1. Patent Document 1 describes that an acetonitrile reagent used for manufacturing medicines, agrochemical, etc. is used as a protecting agent, and a protecting group can be efficiently introduced into the hydroxy group under a mild reaction condition like slight acidity.

PRIOR ART DOCUMENT

Patent Document

Patent Document 1: WO/2005/014508

BRIEF SUMMARY OF THE INVENTION

Problems the Invention Intends to Solve

However, the technique described in Patent Document 1 is protection of a hydroxy group by an acetal-type protecting group, and the advantage of the protection by the above-described benzyl group may be vitiated. That is, since an acetal structure is easily hydrolyzed under an acidic condition, both a hydroxy group-protecting reagent (synonymous with the hydroxy group-protecting agent) and derivatives in which an alcohol is protected by this are considered to be unstable against acids. On the other hand, since the benzyl group is stable under either acidic or basic condition, such a problem is not caused. In addition, there is fear that an allyl-halogen structure contained in the hydroxy group-protecting reagent for use and α-haloketones caused after introduction of the protecting group have carcinogenicity, tearing property, toxicity, etc., like a halogenated benzyl.

The present invention is proposed in light of such actual circumstances, its purpose is to provide an inexpensive hydroxy group-protecting agent which is stable and easy to use and does not have carcinogenicity, toxicity, tearing property, etc., and furthermore provide a hydroxy group protection method therewith. Also, the purpose of the present invention is to provide a hydroxy group-protecting agent and a hydroxy group protection method for protecting a hydroxy group under an acidic condition.

Means for Solving the Problems

The inventors have conducted various researches multiple times in order to achieve the above purposes. As results, it was found that a compound in which a protecting group bound to an electron-attractive heterocyclic ring containing nitrogen such as 2,4,6-tribenzyloxy-1,3,5-triazine could protect a hydroxy group under an acidic condition while being a stable compound, leading to conception of the present invention.

That is, the hydroxy group-protecting agent of the present invention is characterized in that one or more protecting groups bind to the electron-attractive heterocyclic ring containing nitrogen through any of oxygen atoms, sulfur atoms and nitrogen atoms. In addition, the hydroxy group protection method of the present invention is characterized in that the hydroxy group-protecting agent in which one or more protecting groups bind to the electron-attractive heterocyclic ring containing nitrogen through any of oxygen atoms, sulfur atoms and nitrogen atoms is activated on an objective compound having the hydroxy group under an acidic condition to protect the hydroxy group by the protecting group.

In the compound in which one or more protecting groups bind to the electron-attractive heterocyclic ring containing nitrogen through any of oxygen atoms, sulfur atoms and nitrogen atoms, the reaction of the protecting group with the hydroxy group progresses by electron-attracting effects of the heterocyclic ring under an acidic condition, and formation of an inactive structure can be achieved. I.e. efficient protection of the hydroxy group can be achieved.

The hydroxy group-protecting agent of the present invention is a solid which is stable even in air and its material is inexpensive. Also, since it is not lachrymatory and comprises no halogen as a constituent element, it is expected to reduce problems of facilities for use and disposal of a waste liquid, and the risk of the carcinogenicity. Furthermore, one or more protecting groups can bind to the heterocyclic ring, for example if a compound having three protecting groups is used, all of the three protecting groups can be used, and efficient protection of the hydroxy group can be achieved.

In addition, for the hydroxy group-protecting agent of the present invention, the protecting group can be optionally selected, e.g. it is not limited to an acetal-type protecting group like the invention described in Patent Document 1, and the hydroxy group can be protected by benzylation or the like. Consequently, taking the benzylation as an example, the above-described advantages of the benzyl group can be utilized as they are.

Effects of the Invention

According to the present invention, it is possible to provide an inexpensive hydroxy group-protecting agent which is stable and easy to use, not lachrymatory, and is expected to reduce problems of facilities for use and disposal of the waste liquid, and the risk of the carcinogenicity. In addition, it is possible to provide a hydroxy group-protecting agent and a hydroxy group protection method which allow protection of the hydroxy group under an acidic condition.

MODE FOR CARRYING OUT THE INVENTION

Hereinafter, embodiments of the hydroxy group-protecting agent and the hydroxy group protection method to which the present invention was applied will be detailed.

First, the hydroxy group-protecting agent of the present invention is characterized in that one or more protecting groups bind to the electron-attractive heterocyclic ring containing nitrogen through any of oxygen atoms, sulfur atoms and nitrogen atoms, as described above.

That is, the structure of the hydroxy group-protecting agent is as shown in the following Formula 4.

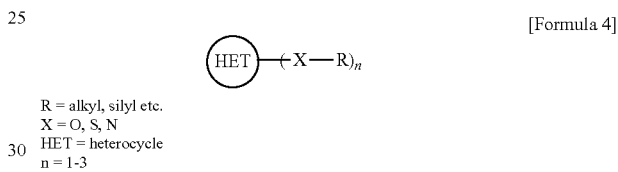

[Formula 4]

R = alkyl, silyl etc.
X = O, S, N
HET = heterocycle
n = 1-3 wherein, HET represents a heterocyclic ring, and X represents any of O, S and N. R is a protecting group, and n is an integer of 1-3.

Herein, the electron-attractive heterocyclic ring containing nitrogen comprises nitrogen, has conjugated unsaturated bonds, and can adopt any structure of electron-attractive heterocyclic rings, for example, a six-membered ring or a five-membered ring. Preferably, it can be exemplified by a triazine ring having three nitrogen atoms, a pyrimidine ring having two nitrogen atoms and the like, and the triazine ring is most preferable, for a reason that it can bind to three protecting groups and other reasons.

Meanwhile, the protecting group binding to the heterocyclic ring may be any protecting group capable of inactivating the hydroxy group, and can be exemplified by a benzyl group having a benzyl group or its substituent, an aryl group, a tertiary alkyl group, etc.

The protecting group must bind to the heterocyclic ring containing nitrogen through any of oxygen atoms, sulfur atoms and nitrogen atoms, and for example, when the protecting group is a butyl group, the butyl group structurally binds to the heterocyclic ring through oxygen atoms or the like. In a case of the nitrogen atoms, the protecting group is structurally linked to the heterocyclic ring through an amino group.

As a representative example of the hydroxy group-protecting agent of the present invention, a 2,4,6-tris(t-butoxy)-1,3,5-triazine is shown in the following Formula 5. The 2,4,6-tris(t-butoxy)-1,3,5-triazine is in a form that three butyl groups bind to the triazine ring through oxygen atoms, as shown in the following Formula 5.

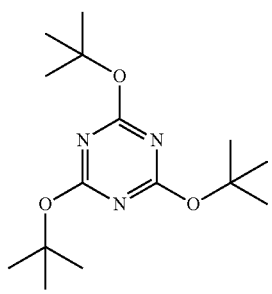

[Formula 5]

It should be noted that, in the 2,4,6-tris(t-butoxy)-1,3,5-triazine, the number of the t-butoxy groups binding to the triazine ring is not limited to three, and may be one or two. In that case, any substituent other than the t-butoxy group may bind to there. Furthermore, the t-butoxy group has a structure that three methyl groups bind to the carbon atoms linked to the oxygen atoms, wherein this methyl group may be any substituent, and the number and the combination of the substituent are also optional. Examples of the substituent may include hydrogen, a halo group, a methyl group, an ethyl group, a linear or branched/cyclic alkyl group with a length longer than propyl, an alkenyl group having vinyl or its substituent, an alkynyl group having an ethynyl group or its substituent, a phenyl group having a phenyl group or its substituent, a polycyclic aryl group having a naphthyl group or a pyrenyl group, an aromatic heterocyclic group having a pyridyl group, a thiophenyl group or the like, an alkyloxy group such as a methoxy group and a benzyloxy group, an alkylthio group, etc. For example, substitution by three phenyl groups forms a triphenylmethyl group (trityl group). Substitution by a phenyl group, a methyl group and hydrogen forms a 1-phenethyl group. Substitution by a methoxy group and two hydrogen atoms forms a methoxymethyl group (MOM group). Substitution by a phenyl group and two hydrogen atoms forms a benzyl group. Substitution by 4-methoxyphenyl group and two hydrogen atoms forms a methoxybenzyl group. Substitution by a vinyl group and two hydrogen atoms forms an allyl group. Substitution by an ethynyl group and two hydrogen atoms forms a propargyl group. Thus, any substituent can be selected as required.

For example, if the protecting group is a benzyl group, the protecting group has a structure that the benzyl group binds to the heterocyclic ring through oxygen atoms or the like. A general formula of the hydroxy group-protecting agent in a case that the heterocyclic ring is a triazine ring and the protecting group is a benzyl group is shown in Formula 6. In light of stability, easiness of the deprotection, easiness of the purification after the deprotection, etc., the benzyl group is preferable as the protecting group.

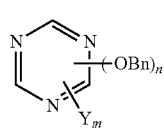

[Formula 6]

wherein, Bn represents benzyl group and Y represents any substituent. When a plurality of Y bind to there, they may be the same substituents or different from each other. n is an integer of 1-3, and m≤(3−n).

As a representative example of the hydroxy group-protecting agent in which the heterocyclic ring is a triazine ring and the protecting group is a benzyl group, a 2,4,6-tribenzyloxy-1,3,5-triazine is shown in the following Formula 7. The 2,4,6-tribenzyloxy-1,3,5-triazine is in a form that three benzyl groups bind to the triazine ring through oxygen atoms, as shown in the following Formula 7.

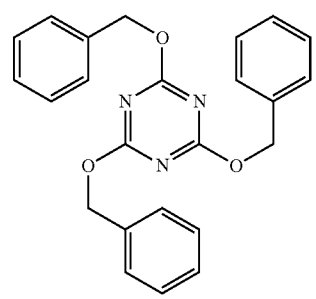

[Formula 7]

It should be noted that each phenyl group may have any substituent, in the 2,4,6-tribenzyloxy-1,3,5-triazine. In addition, the number of the benzyloxy groups binding to the triazine ring is not limited to three, and may be one or two. In that case, any substituent other than the benzyloxy group may bind to there.

As the hydroxy group-protecting agent, not only the above-mentioned compounds but also the 2,4,6-tris(4-methoxybenzyloxy)-1,3,5-triazine represented by Formula 8, the 2,4,6-tris(propargyloxy)-1,3,5-triazine represented by Formula 9, a 2,4,6-tris(alkyloxy)-1,3,5-triazine represented by Formula 10, etc. can also be used.

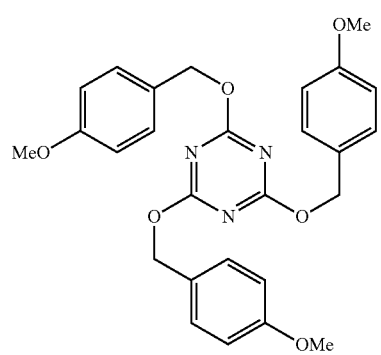

[Formula 8]

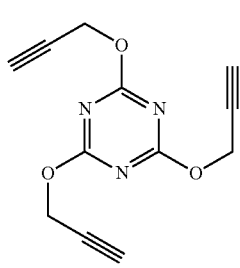

[Formula 9]

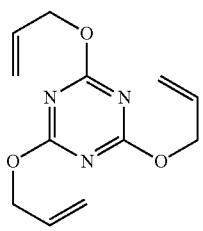

The hydroxy group which disturbs synthetic reaction is protected and inactivated using the above-described hydroxy group-protecting agent, and the condition in this case is an acidic condition. The objective compound having the hydroxy group should be reacted with the hydroxy group-protecting agent under an acidic condition. Although any catalyst can be used as an acid catalyst, trifluoromethane-sulfonic acid and the like is preferable. A reaction formula in the case that the 2,4,6-tris(4-butoxy)-1,3,5-triazine is used as the hydroxy group-protecting agent, and a reaction formula in the case that the 2,4,6-tribenzyloxy-1,3,5-triazine is used as the hydroxy group-protecting agent are shown in Formula 11 and Formula 12 respectively.

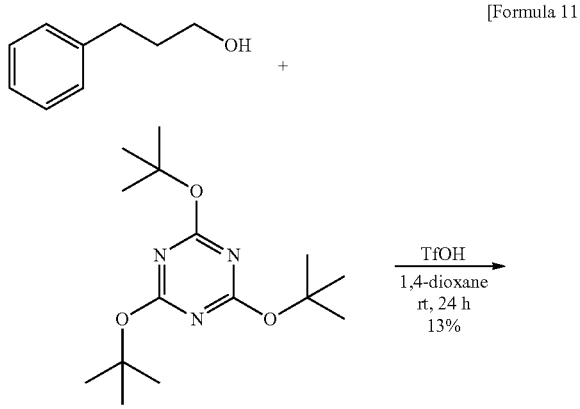

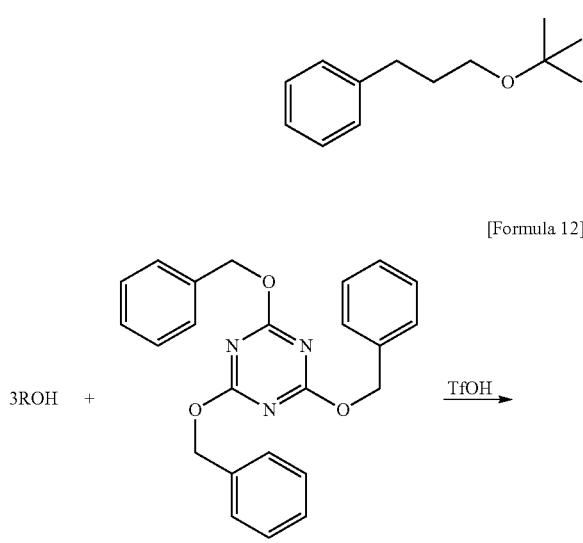

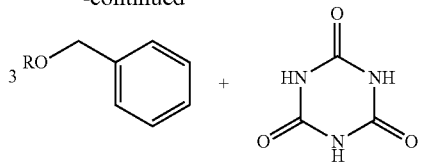

The reactions are conducted in a solvent. As the solvent, a nonaqueous solvent which is inactive to hydroxy groups, hydroxy group-protecting agents and acid catalysts may be used, for example dioxane or the like can be used. Additionally, for the reaction, commingling water is preferably eliminated, for example, a dehydrating agent such as a molecular sieve is preferably mixed.

For reaction, the objective compound and the hydroxy group-protecting agent should be added so that a ratio of the hydroxy group and the protecting group is 1:1, and for example, when the 2,4,6-tris(4-butoxy)-1,3,5-triazine and the 2,4,6-tribenzyloxy-1,3,5-triazine are used as hydroxy group-protecting agents, 1 mol of the 2,4,6-tris(4-butoxy)-1,3,5-triazine or the 2,4,6-tribenzyloxy-1,3,5-triazine may be added with respect to 3 mol of the objective compound having one hydroxy group. Needless to say, even if the ratio of the protecting group becomes excessive, any problems are not caused.

As a concept, the hydroxy group to be protected includes not only what we call hydroxy group but also e.g. a hydroxy group moiety of a carboxyl group, etc. in the present invention.

As described above, the hydroxy group-protecting agent of the present invention is excellent in stability, easy to use, does not have carcinogenicity, tearing property, etc., and is excellent in practicality. According to the hydroxy group-protecting agent of the present invention, a protecting group can be introduced under an acidic condition, for example, the agent can also be applied to protection of the objective compound instable to bases, etc.

EXAMPLES

Hereinafter, specific examples to which the present invention was applied will be explained on the basis of the experimental results.

Protection of the Hydroxy Group Using 2,4,6-tribenzyloxy-1,3,5-triazine

Using a diethylene glycol monomethyl ether (Objective compound 1) represented by the following Formula 13 as a hydroxy group-containing compound to be protected, protection of the hydroxy group by the 2,4,6-tribenzyloxy-1,3,5-triazine was attempted. Note that the 2,4,6-tribenzyloxy-1,3, 5-triazine can be synthesized by a method described in a literature (Literature: K. Srinivas, S. Sitha, V. J. Rao, K. Bhanup rakash, K. Ravikumar, J. Mater. Chem. 2006, 16, 496-504).

[Formula 13]

The reaction was conducted as described below. That was, an activated powdery molecular sieve 5A (62.5 mg), 58.9 µL (0.500 m mol) of diethylene glycol monomethyl ether, 69.9 mg (0.175 m mol) of 2,4,6-tribenzyloxy-1,3,5-triazine (TBnO-T), 15.4 µL (0.175 m mol) of trifluoromethane sulfonic acid (TfOH), and 2.50 mL of 1,4-dioxane were added to a test tube, and reacted at room temperature under a nitrogen atmosphere for 160 minutes.

After the reaction, sodium hydrogen carbonate was added, and stirred for 30 minutes, from which 1,4-dioxane was distilled away. To the residue, 10 mL of ethyl acetate was added, filtered by Celite, and then washed with 5 mL of saturated salt water. A resulting organic phase was dried by sodium sulfate, from which ethyl acetate was then distilled away, and the residue was isolated and purified by silica-gel chromatography to obtain 103 mg of diethylene glycol benzylmethyl ether (yield: 98%).

According to the above-described method, the hydroxy group of diethylene glycol monomethyl ether was protected under Reaction condition A (TBnO–T=0.60 eq., TfOH=0.20 eq.) and Reaction condition B (TBnO–T=0.35 eq., TfOH=0.35 eq.). In order to evaluate whether the acid functions at a catalytic amount, the ratio of TBnO–T and TfOH was changed between Reaction condition A and Reaction condition B. In both conditions, the diethylene glycol benzylmethyl ether could be obtained at high yields. Particularly, in the later condition, it was revealed that the side effects could be reduced, and all of three benzyl groups constituting the 2,4,6-tribenzyloxy-1,3,5-triazine were effectively used.

Also in relation to the objective compounds 2-6 having other hydroxy groups, protection of the hydroxy group was attempted by the same method. The objective compounds are as shown in Table 1. In Table 1, the yields in each condition are also shown together. It should be noted that, in relation to the case of No. 3 compound of the objective compounds shown in Table 1, the protecting group could be introduced in a high yield, even when the Reaction condition B was changed to TBnO–T=0.40 eq. and TfOH=0.40 eq. (yield: 94%).

TABLE 1

| Objective Compound No. | Structure of Objective Compound | Yield (%) Condition A | Yield (%) Condition B |
|---|---|---|---|
| 1 | HO~~O~~O~ | 94 | 98 |
| 2 | Ph~~~OH | 89 | 90 |
| 3 | AcO~~~~~~~~~OH | 91 | 86 |
| 4 | menthol structure (Me, OH, iPr cyclohexane) | 73 | 88 |
| 5 | PhCH(Me)OH | — | 65 |
| 6 | 1-adamantanol | 88 | 78 |

In all of the objective compounds, benzylated compounds could be obtained in a high yield, and thus it was confirmed that the 2,4,6-tribenzyloxy-1,3,5-triazine was useful as a hydroxy group-protecting agent.

Example 1 of Synthesis of Hydroxy Group-Protecting Agent

Cyanuric chloride and chloro dimethoxy triazine (CDMT) or 2,4,6-tribenzyloxy-1,3,5-triazine were used as materials to synthesize hydroxy group-protecting agents 1-5. The synthesis pathways are as shown in the following Formula 14,

[Formula 14]

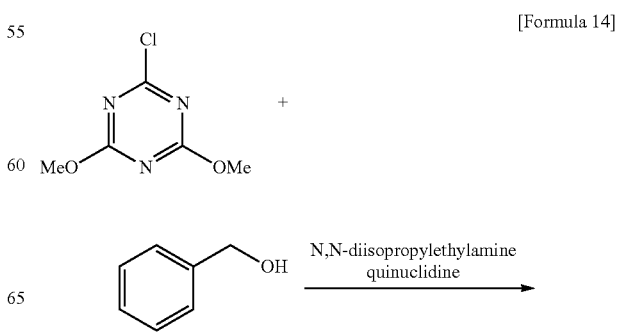

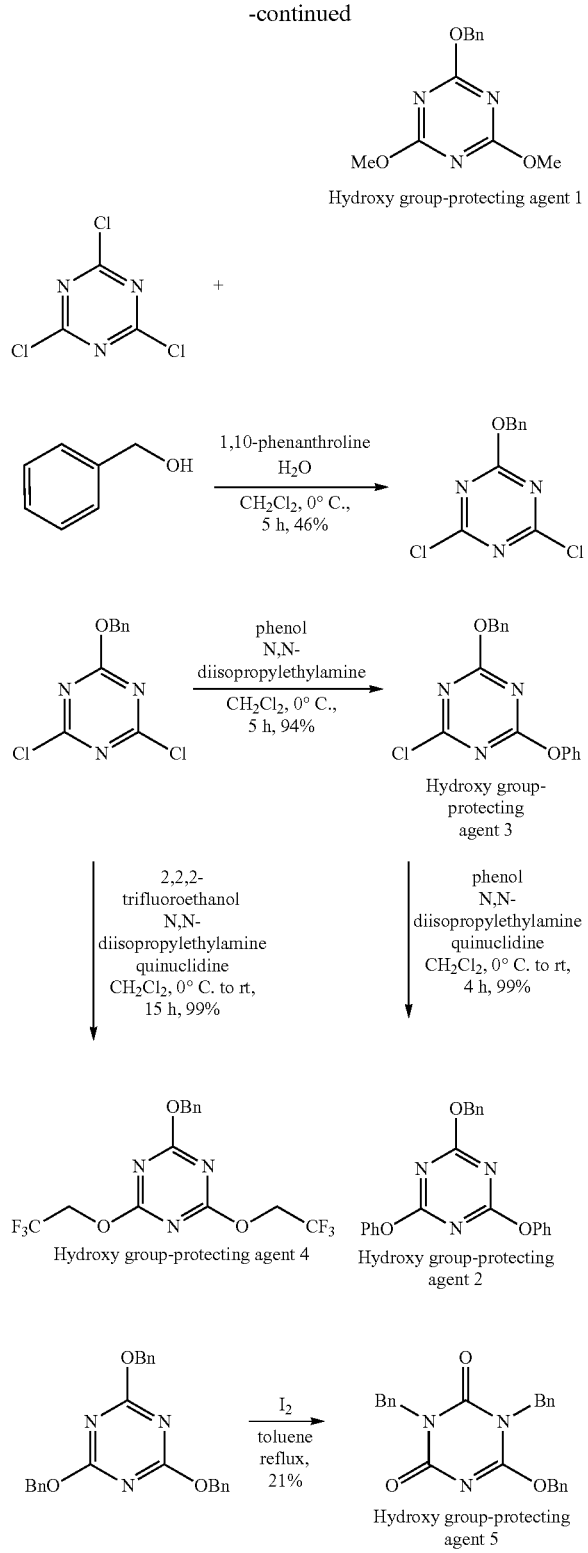

Hydroxy group-protecting agent 1

Hydroxy group-protecting agent 3

Hydroxy group-protecting agent 4

Hydroxy group-protecting agent 2

Hydroxy group-protecting agent 5

First, a synthesis method of the hydroxy group-protecting agent 3 will be explained. An activated molecular sieve 4A, 54.1 μL (0.525 m mol) of benzyl alcohol, 118.9 mg (0.600 m mol) of 1,10-phenanthroline hydrate, 1.00 mL of dichloromethane, 92.2 mg (0,500 m mol) of cyanuric chloride were added to a test tube, and reacted at 0 degree under a nitrogen atmosphere for 5 hours. After the reaction, a precipitate was filtered, and 20 mL of ethyl acetate was added to the filtrate, which was washed with 10 mL of an aqueous solution of saturated sodium hydrogen carbonate, 5 mL of water, 10 mL of 1 N hydrochloric acid, 5 mL of water and 10 mL of saturated salt water. A resulting organic phase was dried by magnesium sulfate, from which ethyl acetate was distilled away, and the residue was isolated and purified by silica-gel chromatography to obtain 58.9 mg of 6-benzyloxy-2,4-dichloro-1,3,5-triazine (yield: 46%).

Next, 5.70 mL of dichloromethane solution containing 896.2 mg (3.50 m mol) of 6-benzyloxy-2,4-dichloro-1,3,5-triazine, 2.00 mL of dichloromethane, 365.0 mg (3.88 m mol) of phenol and 0.738 mL (4.23 m mol) of N,N-diisopropylethylamine was added to a 30 mL eggplant flask, and reacted at 0 degree under a nitrogen atmosphere for 6 hours. After the reaction, 20 mL of dichloromethane was added, which was washed with 20 mL of 1 N hydrochloric acid, 20 mL of 1 N hydrochloric acid, 20 mL of water and 20 mL of saturated salt water. A resulting organic phase was dried by magnesium sulfate, from which dichloromethane was distilled away, and the residue was recrystallized to obtain 1033.2 mg of 6-benzyloxy-2-chloro-4-phenoxy-1,3,5-triazine (yield: 94%).

Next, a synthesis method of the hydroxy group-protecting agent 2 will be explained. To a 30 mL eggplant flask, 470.6 mg (1.50 m mol) of 6-benzyloxy-2-chloro-4-phenoxy-1,3,5-triazine, 3.00 mL of dichloromethane, 178.8 mg (1.90 m mol) of phenol and 0.390 mL (1.90 m mol) of N,N-diisopropylethylamine were added, and reacted at 0 degree under a nitrogen atmosphere for 4 hours. After the reaction, 50 mL of dichloromethane was added, which was washed with 20 mL of 1 N hydrochloric acid, 20 mL of 1 N hydrochloric acid, 20 mL of water and 20 mL of saturated salt water. A resulting organic phase was dried by magnesium sulfate, from which dichloromethane was distilled away to obtain 548.5 mg of 6-benzyloxy-2,4-diphenoxy-1,3,5-triazine (yield: 99%).

Furthermore, a synthesis method of the hydroxy group-protecting agent 5 will be explained. To a 10 mL eggplant flask, 599.2 mg (1.50 m mol) of 2,4,6-tribenzyloxy-1,3,5-triazine, 5.00 mL of toluene and 38.8 mg (030 m mol) of iodine were added, heat-perfused, and reacted for 31 hours. After the reaction, 5 mL of an aqueous solution of saturated sodium thiosulfate was added, which was washed with 5 mL of 1 N sodium bicarbonate water, 5 mL of 1 N hydrochloric acid, 5 mL of water and 5 mL of saturated salt water. A resulting organic phase was dried by magnesium sulfate, from which the solvent was distilled away, and the residue was isolated and purified by silica-gel chromatography to obtain 126.2 mg of 1,3-dibenzyl-6-(benzyloxy)-1,3,5-triazine-2,4(1H,3H)-dione (yield: 21%).

Protection of the Hydroxy Group by the Synthesized Hydroxy Group-Protecting Agents 1-5

The objective compound 2 was used as an objective compound having a hydroxy group to protect the hydroxy group according to the protection of the hydroxy group by the 2,4,6-tribenzyloxy-1,3,5-triazine. However, a reaction condition was set to the hydroxy group-protecting agent=1.2 eq., and TfOH=0.2 eq. In addition, for a solvent, dichloromethane was used. In relation to the hydroxy group-protecting agent 5, the condition was set to the hydroxy group-protecting agent=0.35 eq., and TfOH=0.35 eq. In addition, for a solvent, 1,4-dioxane was used. The results are shown in Table 2.

TABLE 2

| Hydroxy group-protecting agent No. | Hydroxy group-protecting agent Short Name | Hydroxy group-protecting agent Structure | Yield(%) (NMR) |
|---|---|---|---|
| 1 | BnO-DMT | 2,4-dimethoxy-6-(benzyloxy)-1,3,5-triazine | 13 |
| 2 | BnO-DPT | 2,4-diphenoxy-6-(benzyloxy)-1,3,5-triazine | 8 |
| 3 | BnO-CPT | 2-chloro-4-phenoxy-6-(benzyloxy)-1,3,5-triazine | 2 |
| 4 | BnO-DTFET | 2,4-bis(2,2,2-trifluoroethoxy)-6-(benzyloxy)-1,3,5-triazine | 7 |
| 5 | BnO-NNDBT | 1,3-dibenzyl-5-(benzyloxy)-... | 28 |

As revealed from Table 2, it was proven that although the yield was low, the hydroxy group could be protected under an acidic condition in all cases using the hydroxy group-protecting agents.

Example of Synthesis of Hydroxy Group-Agent2

The hydroxy group-protecting agents 6, 7 and 8 were synthesized using cyanuric chloride as a material. These hydroxy group-protecting agents can be synthesized with reference to the method described in the following literature, and their synthesis pathways are as shown in the following Formula 15. In addition, an allylating agent (2,4,6-tris(allyloxy)-1,3,5-triazine, Tri-AllylOT) as the hydroxy group-protecting agent 9 was purchased from Tokyo Chemical Industry Co., Ltd. (TCI, product code: TO333). (Literature: K. Srinivas, S. Sitha, V. J. Rao, K. Bhanuprakash, K. Ravikumar, J. Mater. Chem. 2006, 16, 496-504)

-continued

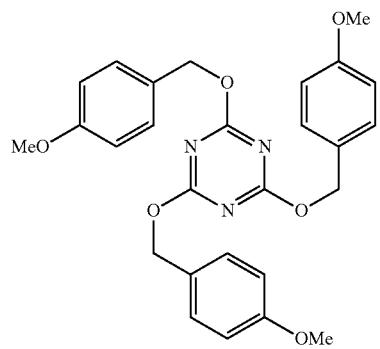

Hydroxy group-protecting agent 6

[Formula 15]

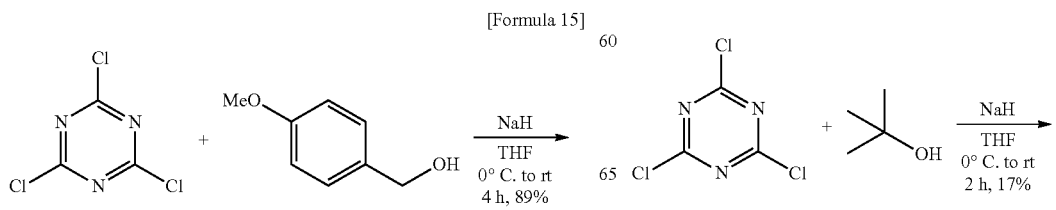

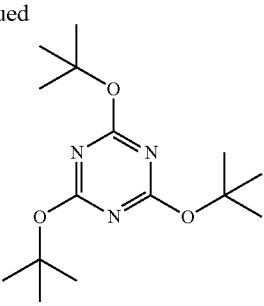

Hydroxy group-protecting agent 7

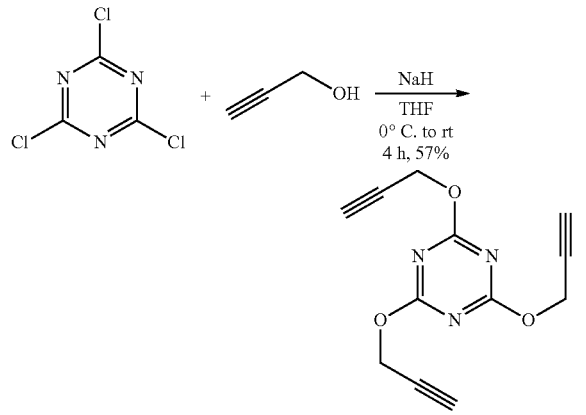

Hydroxy group-protecting agent 8

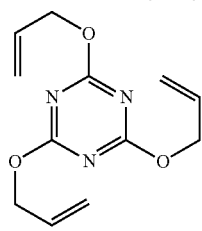

Hydroxy group-protecting agent 9

First, a synthesis method of the hydroxy group-protecting agent 6 will be explained. To a 1 L three-necked eggplant flask, 8.64 g (216 m mol) of 60% sodium hydroxide was added, and suspended in 360 mL of THF under a nitrogen atmosphere. It was cooled to 0° C., to which 24.4 mL (198 m mol) of p-anisyl alcohol was dripped, then heated to room temperature, and stirred for 50 minutes. It was cooled to 0° C., to which a THF solution (100 mL) containing 11.1 g (60 m mol) of cyanuric chloride was dripped for 30 minutes. It was washed with 20 mL of THF, heated to room temperature, and reacted for another 3 hours. After the reaction, the reaction solution was added to 2.4 L of ice chilled water, and the resulting precipitate was filtered off. The solid obtained by filtration was washed with 200 mL of water twice, 100 mL of hexane twice and 200 mL of water once. This solid was dissolved in methylene chloride, filtered by Celite, and then the solvent was distilled away. The solid was recrystallized from 25 mL of methylene chloride and 75 mL of methanol to obtain 29.4 g of 2,4,6-tris(4-methoxybenzyloxy)-1,3,5-triazine (yield: 89%).

Next, a synthesis method of the hydroxy group-protecting agent 7 will be explained. To a 500 mL eggplant flask, 4.32 g (108 m mol) of 60% sodium hydroxide was added, and suspended in 180 mL of THF under a nitrogen atmosphere. It was cooled to 0° C., to which 9.4 mL (99 m mol) of t-butyl alcohol was dripped, then heated to room temperature and stirred for one hour. It was cooled to 0° C., to which a THF solution (60 mL) containing 5.53 g (30 m mol) of cyanuric chloride was dripped for 3 minutes. It was heated to room temperature, and then reacted for another 1.5 hours. After the reaction, the reaction solution was added to 2.4 L of ice chilled water, and the resulting precipitate was filtered off. The solid obtained by filtration was dissolved in acetone, and the solvent was distilled away. This solid was dissolved in ethyl acetate, and washed with water and saturated salt water. A resulting organic phase was dried by magnesium sulfate, from which ethyl acetate was then distilled away, and the residue was isolated and purified by silica-gel chromatography to obtain 1.38 g of 2,4,6-tris(t-butoxy)-1,3,5-triazine (yield: 17%).

Furthermore, a synthesis method of the hydroxy group-protecting agent 8 will be explained. To a 200 mL eggplant flask, 1.44 g (36 m mol) of 60% sodium hydroxide was added, and suspended in 60 mL of THF under a nitrogen atmosphere. It was cooled to 0 degC, to which 1.9 mL (33 m mol) of propargyl alcohol was dripped, then heated to room temperature and stirred for 60 minutes. It was cooled to 0 degC, to which a THF solution (20 mL) containing 1.84 g (10 m mol) of cyanuric chloride was dripped for 3 minutes. It was heated to room temperature, and then reacted for 1 hour. After the reaction, the reaction solution was added to 800 mL of ice chilled water, and the resulting precipitate was filtered off. The solid obtained by filtration was dissolved in acetone, and the solvent was distilled away. This solid was dissolved in ethyl acetate, and washed with water and saturated salt water. A resulting organic phase was dried by magnesium sulfate, from which ethyl acetate was then distilled away, and the residue was isolated and purified by silica-gel chromatography to obtain 1.38 g of 2,4,6-tris(propargyloxy)-1,3,5-triazine (yield: 57%).

Protection of the Hydroxy Group Using 2,4,6-tris(4-methoxybenzyloxy)-1,3,5-triazine (Hydroxy Group-Protecting Agent 6)

Using 2-trimethylsilylethanol represented by the following Formula 16 as a hydroxy group-containing compound to be protected, protection of the hydroxy group by the 2,4,6-tris(4-methoxybenzyloxy)-1,3,5-triazine was attempted.

[Formula 16]

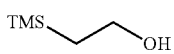

The reaction was conducted as described below. That was, 142 μL (1.00 m mol) of 2-trimethylsilylethanol was added to a test tube, and dissolved in 1.50 mL of ethyl acetate. Dripping of 195.8 mg (0.40 m mol) of the 2,4,6-tris(4-methoxybenzyloxy)-1,3,5-triazine dissolved in 2.2 mL of ethyl acetate was started at room temperature under nitrogen atmosphere, and immediately after that, 30 μL of ethyl acetate solution containing trifluoromethane sulfonic acid (TfOH) (100 mM) was added. The dripping was conducted for 10 minutes, and after the dripping, the mixture was reacted for 5 minutes.

After the reaction, the reactant was washed with 5 mL of an aqueous solution of saturated sodium hydrogen carbonate and 5 mL of water, and the aqueous phases were re-extracted by 5 mL of ethyl acetate and washed with 5 mL of saturated salt water. A resulting organic phase was dried by magnesium sulfate, from which ethyl acetate was distilled away, and the residue was isolated and purified by silica-gel chromatography to obtain 198.3 mg of 2-trimethyl-1-(4-methoxybenzyloxy) ethane (yield: 83%).

According to the above-described method, the hydroxy group of the 3-phenyl-1-propanol represented by Formula 17 was protected in various reaction conditions 1-13 shown in Table 3.

TABLE 3

| Condition | Solvent | Acid Catalyst (mol %) | Temperature | Reaction time | Yield (%)[a] |
|---|---|---|---|---|---|
| 1 | 1,4-dioxane | TfOH(1) | Room Temp. | 5 min. | 91 |
| 2 | 1,4-dioxane[b] | TfOH(1) | Room Temp. | 5 min. | 95 |
| 3 | 1,4-dioxane | TfOH(0.1) | Room Temp. | 1 hour | 90 |
| 4 | methylene chloride | TfOH(0.3) | Room Temp. | 15 min. | 66 |
| 5 | methylene chloride-diethyl ether (9:1) | TfOH(0.3) | Room Temp. | 15 min. | 85 |
| 6 | ethyl acetate | TfOH(0.3) | Room Temp. | 15 min. | 94 |
| 7 | ethyl acetate | BF3•Et2O(5) | Room Temp. | 25 min. | 89 |
| 8 | toluene | BF3•Et2O(3) | Room Temp. | 20 min. | 88 |
| 9 | 1,2-dimethoxyethane | CSA(20) | Room Temp. | 4.5 day | 79 |
| 10 | 1,2-dimethoxyethane | Sulfate(20) | 0 deg C. | 1 hour | 65 |
| 11 | 1,2-dimethoxyethane | Sc(OTf)3(1) | Room Temp. | 20 min. | 91 |
| 12 | 1,2-dimethoxyethane | BF3•Et2O(3) | Room Temp. | 20 min. | 92 |
| 13 | 1,2-dimethoxyethane | TfOH(1) | 0 deg C. | 25 min. | 95 |

[a]NMR yield,
[b]added molecular sieves 5A (5 mg/mL)

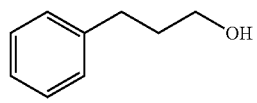

[Formula 17]

When reaction was conducted using 1,4-dioxane as a solvent and trifluoromethane sulfonic acid (TfOH) (1 mol %) as an acid catalyst, the reaction was terminated at room temperature in five minutes, and a desired substance could be obtained in a yield of 91% (Reaction condition 1). In order to eliminate commingling water, molecular sieves 5A were added, and thereby the yield was improved (Reaction condition 2). Even when the TfOH as the acid catalyst was decreased to 0.1 mol %, the reaction was progressed (Reaction condition 3). When the solvent was changed to methylene chloride, the yield was decreased (Reaction condition 4), but when diethyl ether was added as a cosolvent, the yield was increased (Reaction condition 5). Besides, uses of ethyl acetate as an ester solvent (Reaction condition 6), toluene as an aromatic solvent (Reaction condition 8) and 1,2-dimethoxyethan as an ether solvent (Reaction condition 9) could also obtain the desired substance in a good yield, thus the applicable range for the solvents to be used is broad, and the solvent can be changed for purposes.

As the acid catalyst, CSA which is a protic acid weaker than TfOH (Reaction condition 9), sulfuric acid (Reaction condition 10), Sc (OTf) 3 which is a Lewis acid (Reaction condition 11) and BF3.Et20 (Reaction conditions 7, 8, 12) could be used. In addition, even when the reaction temperature was 0° C., the reaction could be progressed (Reaction condition 13).

Protection of the Hydroxy Group Using 2,4,6-tris(t-butoxy)-1,3,5-triazine (Hydroxy Group-Protecting Agent 7)

Using 3-phenyl-1-propanol represented by Formula 17 as a hydroxy group-containing compound to be protected, protection of the hydroxy group by the 2,4,6-tris(t-butoxy)-1,3,5-triazine was attempted.

To a test tube, 40.9 μL (0.300 m mol) of 3-phenyl-1-propanol and 35.7 mg (0.120 m mol) of 2,4,6-tris(t-butoxy)-1,3,5-triazine were added, and dissolved in 1.50 mL of 1,4-dioxane, to which 5.3 μL (0.060 m mol) of trifluoromethane sulfonic acid (TfOH) was added under nitrogen atmosphere at room temperature and reacted for 24 hours.

After the reaction, triethylamine was added, from which 1,4-dioxane was then distilled away. The residue was isolated and purified by silica-gel chromatography to obtain 7.7 mg of 3-phenyl-1-t-butoxypropane (yield: 13%).

Protection of the Hydroxy Group Using 2,4,6-tris(propargyloxy)-1,3,5-triazine (Hydroxy Group-Protecting Agent 8)

Using 3-phenyl-1-propanol represented by Formula 17 as a hydroxy group-containing compound to be protected, protection of the hydroxy group by the 2,4,6-tris(propargyloxy)-1,3,5-triazine was attempted.

To a test tube, 40.9 μL (0.300 m mol) of 3-phenyl-1-propanol and 29.2 mg (0.120 m mol) of 2,4,6-tris(propargyloxy)-1,3,5-triazine were added, and dissolved in 1.50 mL of 1,4-dioxane, to which 5.3 μL (0.060 m mol) of trifluoromethane sulfonic acid (TfOH) was added under nitrogen atmosphere at room temperature, reacted for 20 hours, and then reacted at 60 degC for 18 hours.

After the reaction, triethylamine was added, from which 1,4-dioxane was then distilled away. The residue was isolated and purified by silica-gel chromatography to obtain 4.8 mg of 3-phenyl-1-propargyloxypropane (yield: 9%).

Protection of the Hydroxy Group Using 2,4,6-tris(allyloxy)-1,3,5-triazine (Hydroxy Group-Protecting Agent 9)

Using 3-phenyl-1-propanol represented by Formula 17 as a hydroxy group-containing compound to be protected, protection of the hydroxy group by the 2,4,6-tris(allyloxy)-1,3,5-triazine was attempted.

To a test tube, 40.9 μL (0.300 m mol) of 3-phenyl-1-propanol and 29.9 mg (0.120 m mol) of 2,4,6-tris(allyloxy)-1,3,5-triazine were added, and dissolved in 1.50 mL of 1,4-dioxane, to which 5.3 μL (0.060 m mol) of trifluoromethane sulfonic acid (TfOH) was added under nitrogen atmosphere at room temperature, reacted for 22 hours, and then reacted at 60° C. for 2 hours.

After the reaction, triethylamine was added, from which 1,4-dioxane was then distilled away. The residue was isolated and purified by silica-gel chromatography to obtain 20.6 mg of 3-phenyl-1-allyloxypropane (yield: 39%).

Esterification Reaction of Carboxylic Acid

Using a carboxylic acid as a hydroxy group-containing compound to be protected, esterification by the 2,4,6-tribenzyloxy-1,3,5-triazine was attempted. The reaction formula is shown in Formula 18.

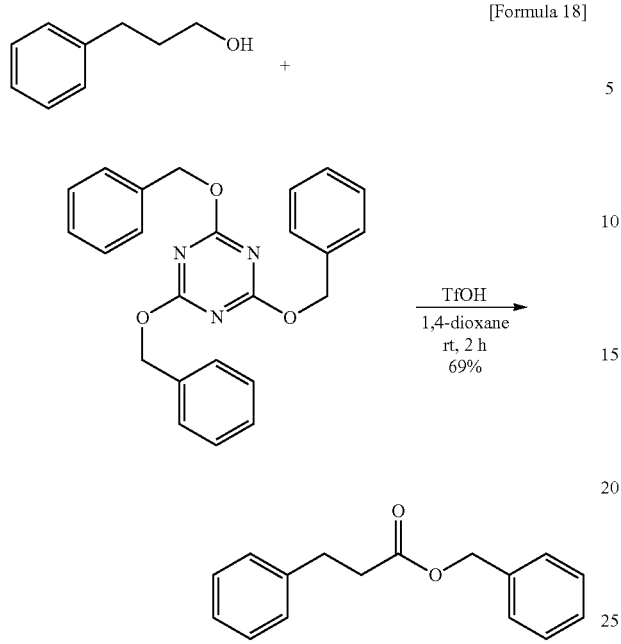

To a test tube, 45.1 mg (0.300 m mol) of 3-phenylpropionic acid and 41.9 mg (0.105 m mol) of 2,4,6-tribenzyloxy-1,3,5-triazine were added, and dissolved in 1.50 mL of 1,4-dioxane, to which 9.2 μL of trifluoromethane sulfonic acid (TfOH) was added under nitrogen atmosphere at room temperature and reacted for 80 minutes, to which 12.0 mg (0.030 m mol) of 2,4,6-tribenzyloxy-1,3,5-triazine was added and reacted for 40 minutes.

After the reaction, triethylamine was added, from which 1,4-dioxane was then distilled away. The residue was isolated and purified by silica-gel chromatography to obtain 50.1 mg of 3-phenylpropionic acid benzyl ester (yield: 69%).

The invention claimed is:

1. A hydroxy group protection method, comprising:
reacting a hydroxy group-protecting agent in which one or more protecting groups bind to a triazine ring containing nitrogen through any of oxygen atoms, sulfur atoms and nitrogen atoms with an objective compound having a hydroxy group under an acidic condition, thereby protecting the hydroxy group of the objective compound by the protecting group,
wherein the hydroxy group-protecting agent is represented in the following formula

[Formula 2]

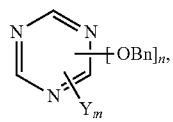

where Bn represents a benzyl group,
Y represents a substituent,
n is an integer of 1-3, and
m ≤ (3−n).

2. The hydroxy group protection method as claimed in claim 1, wherein the hydroxy group-protecting agent is a 2,4,6-tribenzyloxy-1,3,5-triazine represented in the following formula:

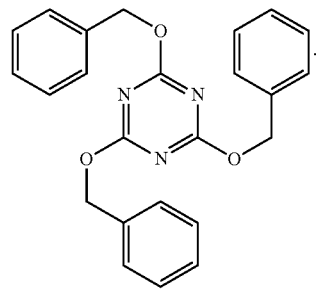 [SMILES: c1ccc(COc2nc(OCc3ccccc3)nc(OCc3ccccc3)n2)cc1]

3. The hydroxy group protection method as claimed in claim 1, wherein the hydroxy group-protecting agent is a 2,4,6-tris(4-methoxybenzyloxy)-1,3,5-triazine represented in the following formula:

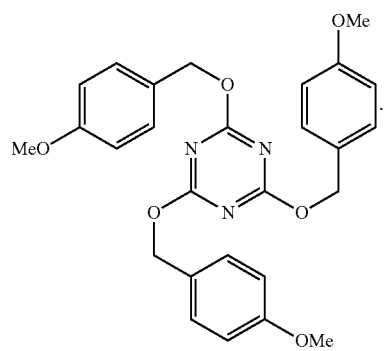 [SMILES: COc1ccc(COc2nc(OCc3ccc(OC)cc3)nc(OCc3ccc(OC)cc3)n2)cc1]

4. The hydroxy group protection method as claimed in claim 1, wherein the hydroxy group-protecting agent is a 2,4,6-tris(t-butoxy)-1,3,5-triazine represented in the following formula:

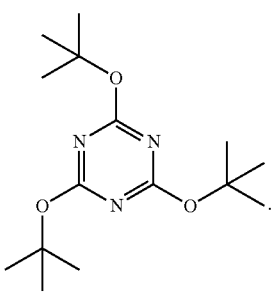 [SMILES: CC(C)(C)Oc1nc(OC(C)(C)C)nc(OC(C)(C)C)n1]

5. The hydroxy group protection method as claimed in claim 1, wherein the hydroxy group-protecting agent is a 2,4,6-tris(propargyloxy)-1,3,5-triazine represented in the following formula:

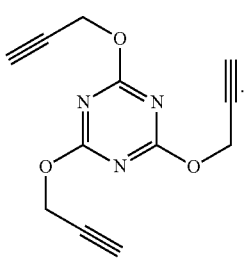 [SMILES: C#CCOc1nc(OCC#C)nc(OCC#C)n1]

6. The hydroxy group protection method as claimed in claim 1, wherein the hydroxy group-protecting agent is a 2,4,6-tris(allyloxy)-1,3,5-triazine represented in the following formula:

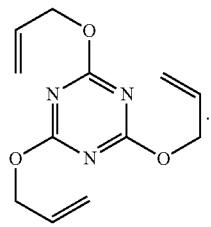 [SMILES: C=CCOc1nc(OCC=C)nc(OCC=C)n1]

7. The hydroxy group protection method as claimed in claim 1, wherein the hydroxy group-protecting agent is represented in the following formula:

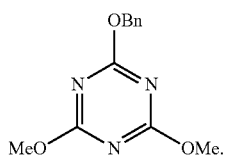

8. The hydroxy group protection method as claimed in claim 1, wherein the hydroxy group-protecting agent is represented in the following formula:

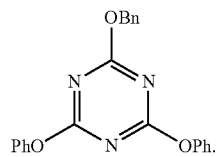

9. The hydroxy group protection method as claimed in claim 1, wherein the hydroxy group-protecting agent is represented in the following formula:

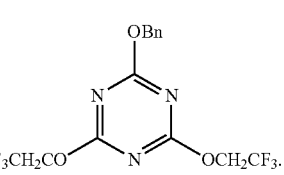

10. The hydroxy group protection method as claimed in claim 1, wherein the hydroxy group-protecting agent is represented in the following formula:

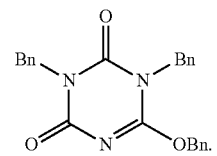

11. The hydroxy group protection method as claimed in claim 1, wherein the hydroxy group-protecting agent is represented in the following formula:

* * * * *